United States Patent [19]

Barmore

[11] 4,068,656
[45] Jan. 17, 1978

[54] ORTHOPEDIC TOENAIL DEVICE

[76] Inventor: Barbara Ann Barmore, Rte. 17, Dewittville, N.Y. 14757

[21] Appl. No.: 728,277

[22] Filed: Sept. 30, 1976

[51] Int. Cl.² ............................................. A61F 5/00
[52] U.S. Cl. ................................................ 128/81 A
[58] Field of Search ........................... 128/81 A, 81 R

[56] References Cited

U.S. PATENT DOCUMENTS

| 1,772,130 | 8/1930 | Crenshaw | 128/81 A |
| 2,567,601 | 9/1951 | Heinhold et al. | 128/81 A |
| 2,632,441 | 3/1953 | Tuve | 128/81 A |

Primary Examiner—John D. Yasko
Attorney, Agent, or Firm—Alan N. McCartney

[57] ABSTRACT

An orthopedic device for relieving the pressure of and correcting ingrown toenails comprising insert means adapted to be positioned under the nail edges adjacent the forward portion of the nail and a resilient member coacting with the insert means and acting on the top portion of the nail and biasing the insert means into and against the nail underside edges. An adjustment means is positioned between the insert means and resilient member to adapt the device to various sized nails and provide an adjustment to increase the pressure applied by the insert means against the nail underside edges.

4 Claims, 7 Drawing Figures

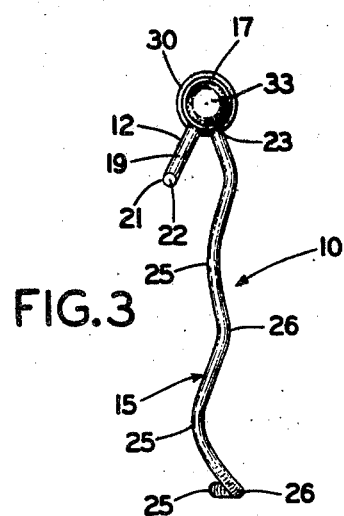
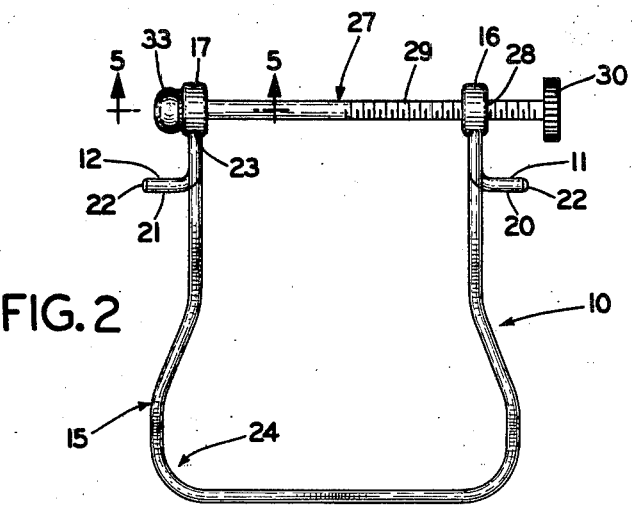
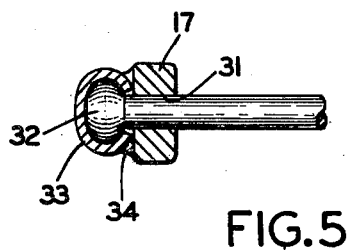
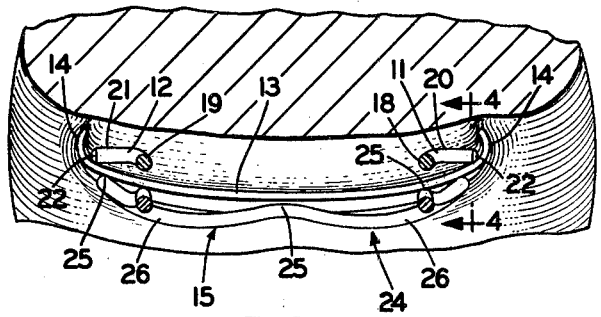
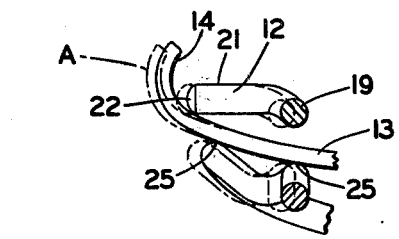
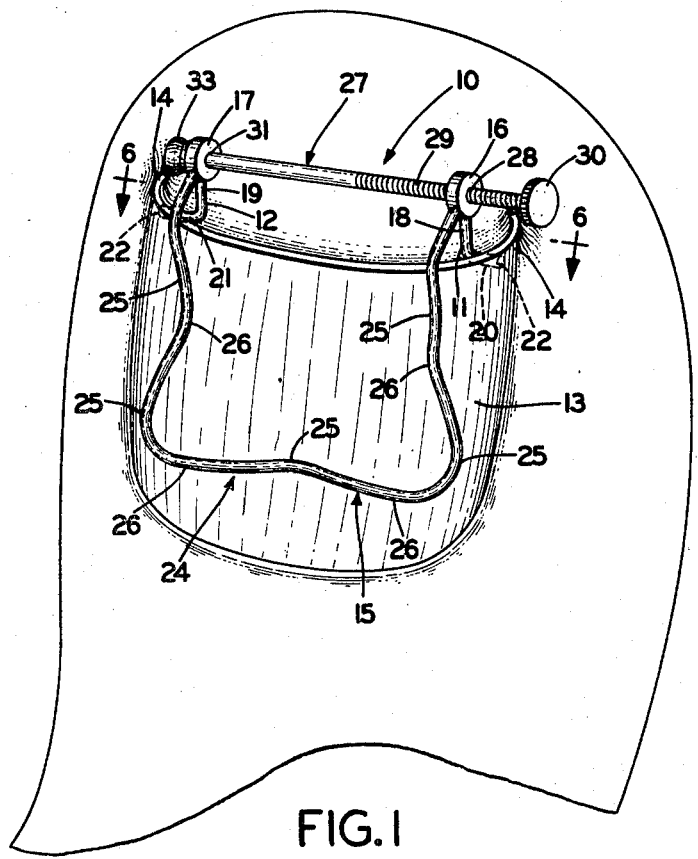
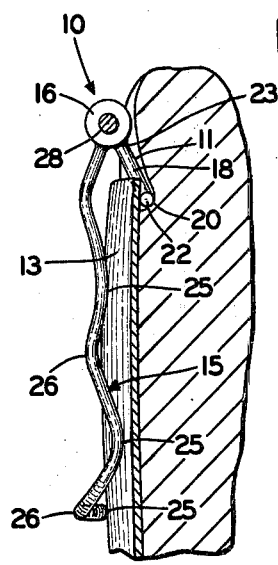

ORTHOPEDIC TOENAIL DEVICE

BACKGROUND OF THE INVENTION

There are a number of ingrown toenail corrective devices in the prior art; however, these devices are all directed to gripping the side edges of the nail. An illustration of such a device is disclosed in U.S. Pat. No. 3,032,032. These devices, however, are basically inoperative. An ingrown toenail results from the side edges of the nail growing downwardly and inwardly into the toe and under the toenail top portion. It is this action of the nail placing pressure on the toe itself that causes the irritation and pain. This resulting growth and position of the nail leaves the side edges of the nail inaccessible to any type of gripping means to reposition the side edges of the nail into the proper location. Thus, devices such as in U.S. Pat. No. 3,032,032 are basically inoperative since the nail side edges when the nail is ingrown are inaccessible.

In view of the nature of the ingrown nail, there is a definite need for a device which can have an insert into the underside of the forward portion of the nail and act on the nail side edges at that location. This is the only location on the nail which is accessible to relieve the pressure on the toe caused by the nail. Further, such a device must be adjustable to various sized nails and adjustable to increase the pressure of the insert means on the nail as the growth of the nail is corrected.

SUMMARY OF THE INVENTION

It is an object of this invention to provide an orthopedic ingrown toenail corrective device which is adjustable to all sizes of nails, is light in weight, comfortable to wear and relieves the pain of and corrects the growth of the ingrown toenail.

It is a further object of this invention to provide an ingrown toenail corrective device having means inserted under the forward underside of the nail which coacts with a resilient means on the top of the nail to continuously apply pressure on the underside of the nail to relieve the pressure of the nail on the toe and position the nail for proper growth.

It is another object of this invention to provide adjustment means for resiliently biased inserts under the nail of an ingrown toenail; such adjustment means permitting varying the pressure on the underside of the nail to relieve pressure and produce proper nail growth and needs no tools for actuation.

It is still another object of this invention to provide a two piece orthopedic device for correcting ingrown toenails which is light in weight, low in profile and small in size so that it can be worn comfortably in any type of shoe apparel.

FIGURES OF THE DRAWING

FIG. 1 is a plan view of the orthopedic device shown in an operative position on a toenail;

FIG. 2 is a plan view of the orthopedic device of this invention;

FIG. 3 is a side elevational view of the device;

FIG. 4 is a side elevational view of the device taken along Line 4—4 of FIG. 1 and illustrating the action of the device on a toenail;

FIG. 5 is an enlarged sectional view taken along the Line 5—5 of FIG. 2;

FIG. 6 is a sectional view taken along the Line 6—6 of FIG. 1; and

FIG. 7 illustrates the action of the insert means and resilient member on the nail when the device is expanded during adjustment.

Reference is now made to the Figures of the drawing which illustrate the orthopedic appliance 10 having inserts 11 and 12 which act on the underside and the forward portion of the nail 13. As previously mentioned and as illustrated in the drawing, the nature of growth of an ingrown toenail results in the side edges of nail as at 14 growing down and under into the toe causing the resulting pressure and pain. With this type of nail growth, the only area of the nail which is accessible to properly position the nail is the forward under portion of the nail. The device of this invention has inserts 11 and 12 acting on the under side of the forward portion of the nail which is the only portion of the nail that is accessible to place pressure on the nail for corrective purposes.

The appliance or device also has a resilient spring steel number 15 coacting with inserts 11 and 12 through interconnecting members 16 and 17. The member 15 and inserts 11 and 12 are integral with connecting members 16 and 17 placing a predetermined and fixed angular relation between inserts 11 and 12 and resilient member 15.

Each of the inserts 11 and 12 are L-shaped and have downwardly extending portions 18 and 19 respectively. The extending portions 18 and 19 have outwardly opposed nail contacting portions 20 and 21 respectively each of which have rounded smooth ends 22 adapted to contact the under forward portion of the nail.

The resilient member 15 is integral with connecting members 16 and 17 as illustrated at 23 and is generally U-shaped as illustrated at 24 in FIGS. 1 and 2. The resilient member 15 also has outwardly extending contact points 25 separated by raised portions 26. Thus, with contacts points 25 and raised portions 26, the member 15 is adapted to contact various points on the upper surface of the nail regardless of the contour of the upper surface of the nail. For example, if the nail upper surface is not a smooth continuous contour, the contact points 25 will still rest on the nail placing the load of member 15 evenly throughout the upper contour of the nail.

Positioned between connecting members 16 and 17 is a threaded adjustment member 27 which has threads 29 threaded into connecting member 16 at 28. The threaded adjustment member 27 has a thumbscrew actuator 30. The adjustment member 27 passes through connecting member 17 at 31 and is freely rotatable therein. Carried on the end of adjustment rod member 27 is a knob 32 adapted to be carried in a socket 33 secured at 34 to connecting member 17. Thus, when adjustment member 27 is actuated by turning thumbscrew 30 the connecting members 16 and 17 and thus inserts 11 and 12 can be moved closer together or further apart as desired.

In application of the appliance 10 to an ingrown toenail, the adjustment member 27 is operated to place the inserts an appropriate distance apart to each be located adjacent the side edges of the forward front portion of the nail. The inserts 11 and 12 are then slid downwardly between the forward side edges of the nail until the nail contact portions 20 and 21 are in contact with the nail. In this position, the resilient member 15 rests on the top surface of the nail through contact points 25. The adjustment screw member 27 is then actuated through thumbscrew 30 to separate inserts 11 and 12. At this point the nail will be deformed as shown at A in FIG. 7 placing a force on inserts 11 and 12 tending to separate 11 and 12 from resilient member 15. This action by the nail tending to change the angular relation of inserts 11 and 12 and member 15 will load member 15 against the top of the nail resulting in inserts 11 and 12 placing a continous outward and upward force on the side edges of the nail to relieve the pressure of the ingrown side edges of the nail and reposition the nail to a proper growth contour. Further, with this action, as the nail returns to its proper growth position, the adjustment member 27 can be actuated to further separate inserts 11 and 12 and further lift the ingrown side edges of the nail away from the toe.

Thus, it can be seen that the operation of the orthopedic appliance of this invention relieves the pain of an ingrown nail and places the nail in position for proper growth and automatically adjusts to such change in growth. Further, the appliance is adjustable without the use of any tools, has few working parts, is light in weight, simple to operate and is low in profile so that it can be worn with any foot apparel. Additionally, with the interaction of the resilient loading member 15 and inserts 11 and 12 through adjustment member 27 the appliance can be utilized on any size of toe.

I claim:

1. An orthopedic appliance for relieving the pain of an ingrown nail and placing the nail in proper position for growth comprising:

a. insert means adapted to act on the forward front underside edges of the nail and free from contact with the top side edges of the nail;

b. resilient means adapted to act on the upper rear surface of the nail;

c. said insert means and resilient means being integral and in fixed angular relation with one another;

c. an adjustment member coacting between said insert means and said resilient means and adapted to separate said insert means against the side edges of the nail tending to load the resilient means and move the nail side edges upward and outward to relieve the pressure of the nail and place the nail in proper position for growth.

2. The orthopedic appliance of claim 1 wherein said insert means and said resilient means are interconnected through button type members and said adjustment member is a thumbscrew acting through said button type members to separate said insert means.

3. The orthopedic device of claim 1 wherein said resilient means is a substantially U-shaped member having end portions connected to each of the insert means, with portions on the U-shaped member adapted to contact the nail surface and with portions raised from the nail surface so that the resilient member will act uniformly on any nail surface regardless the nail surface contour.

4. The orthopedic appliance of claim 2 wherein said adjustment means is threaded into one button member and is freely rotatable and connected with the other button member so that actuation of the adjustment means will separate the insert means.

* * * * *